United States Patent
Ekambaram et al.

(10) Patent No.: US 9,946,636 B2
(45) Date of Patent: Apr. 17, 2018

(54) COMPANION TESTING FOR BODY-AWARE DEVICES

(71) Applicant: International Business Machines Corporation, Armonk, NY (US)

(72) Inventors: Vijay Ekambaram, Chennai (IN); Pratyush Kumar, Chennai (IN); Ashok Pon Kumar Sree Prakash, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 93 days.

(21) Appl. No.: 15/207,242

(22) Filed: Jul. 11, 2016

(65) Prior Publication Data
US 2018/0011782 A1  Jan. 11, 2018

(51) Int. Cl.
*G06F 11/00* (2006.01)
*G06F 11/36* (2006.01)
(Continued)

(52) U.S. Cl.
CPC ........ *G06F 11/3684* (2013.01); *A61B 5/1123* (2013.01); *A61B 5/486* (2013.01);
(Continued)

(58) Field of Classification Search
USPC ................................................. 714/37, 38.1
See application file for complete search history.

(56) References Cited

U.S. PATENT DOCUMENTS 9,152,880 B1 * 10/2015 Moyer ...................... A61B 5/16
2015/0002389 A1 * 1/2015 Lefebvre ............ G06K 9/00335
345/156

(Continued)

FOREIGN PATENT DOCUMENTS

WO    WO2012051654 A1    4/2012

OTHER PUBLICATIONS

Matthew L. Hale et al., "SecuWear: An open source, multi-component hardware/software platform for exploring wearable security", 2015 IEEE International Conference on Mobile Services, 8 pages, IEEE Computer Society, IEEE Digital Library.
(Continued)

*Primary Examiner* — Sarai Butler
(74) *Attorney, Agent, or Firm* — Ference & Associates LLC

(57) ABSTRACT

One embodiment provides a method, including: receiving movement data describing physical movement of a person performing a predetermined action; generating, using a processor, classification of the movement data using a test application that predicts output of a wearable device, wherein the test application has been formed using previously collected data that describe the movement of a person performing the predetermined action; determining, using the processor, whether the movement data match the predetermined action in view of the classification; receiving output of a body-aware application that detects and responds to human movement; comparing, using the processor, the output of the body-aware application with the classification; and providing, using the processor, an indication of the comparing of the output of the body-aware application and the classification.

20 Claims, 4 Drawing Sheets

(51) Int. Cl.
*A61B 5/11* (2006.01)
*A61B 5/00* (2006.01)

(52) U.S. Cl.
CPC ............ *A61B 5/7264* (2013.01); *A61B 5/744* (2013.01); *G06F 11/3688* (2013.01); *G06F 11/3692* (2013.01); *A61B 2560/0475* (2013.01)

(56) References Cited

U.S. PATENT DOCUMENTS

2016/0026560 A1  1/2016  Jackson et al.
2016/0070339 A1* 3/2016  Crawford ................ A61B 5/01
                                                      345/156

OTHER PUBLICATIONS

Jungong Han et al., "Enhanced Computer Vision with Microsoft Kinect Sensor: A Review", IEEE Transactions on Cybernetics, vol. 43, No. 5, Oct. 2013, 17 pages, IEEE Digital Library.

David R. Bassett Jr. et al., "Calibration and Validation of Wearable Monitors", Med Sci Sports Exerc., Jan. 2012, 44 (1 Suppl 1): S32-S38, 13 pages, NIH Public Access.

Randy L. Sollenberger, Ph.D. et al., "Human-in-the-Loop Simulation Evaluating the Collocation of the User Request Evaluation Tool, Traffic Management Advisor, and Controller-Pilot Data Link Communications: Experiment I—Tool Combinations", National Technical Information Service, Springfield, VA, USA, Feb. 2005, DOT/FAA/CT-TN04/28, 84 pages, U.S. Department of Transportation, Federal Aviation Administration, William J. Hughes Technical Center, Atlantic City International Airport, NJ, USA.

* cited by examiner

COMPANION TESTING FOR BODY-AWARE DEVICES

BACKGROUND

Software testing is highly mature and has well developed tools that are used to evaluate the performance of conventional software applications. However, as new devices come into being, such as body-aware devices like smart watches, the testing of body-aware software poses new challenges.

Testing of body-aware applications requires the blending of data from human interaction and behavior and the software's output. Having human input in the loop as a variable complicates the testing process, which leads to challenges in the specification and generation of test cases for human activity modalities, as well as challenges in the two way interaction between a human and the system used to conduct the test.

BRIEF SUMMARY

In summary, one aspect of the invention provides a method, comprising: receiving movement data describing physical movement of a person performing a predetermined action; generating, using a processor, classification of the movement data using a test application that predicts output of a wearable device, wherein the test application has been formed using previously collected data that describe the movement of a person performing the predetermined action; determining, using the processor, whether the movement data match the predetermined action in view of the classification; receiving output of a body-aware application that detects and responds to human movement; comparing, using the processor, the output of the body-aware application with the classification; and providing, using the processor, an indication of the comparing of the output of the body-aware application and the classification.

Another aspect of the invention provides an apparatus, comprising: at least one processor; and a computer readable storage medium having computer readable program code embodied therewith and executable by the at least one processor, the computer readable program code comprising: computer readable program code that receives movement data describing physical movement of a person performing a predetermined action; computer readable program code that generates classification of the movement data using a test application that predicts output of a wearable device, wherein the test application has been formed using previously collected data that describe the movement of a person performing the predetermined action; computer readable program code that determines whether the movement data match the predetermined action in view of the classification; computer readable program code that receives output of a body-aware application that detects and responds to human movement; computer readable program code that compares the output of the body-aware application with the classification of the movement of the companion test application; and computer readable program code that provides an indication of the comparing of the output of the body-aware application and the classification.

An additional aspect of the invention provides a computer program product, comprising: a computer readable storage medium having computer readable program code embodied therewith, the computer readable program code being executable by a processor and comprising: computer readable program code that receives movement data describing physical movement of a person performing a predetermined action; computer readable program code that generates classification of the movement data using a test application that predicts output of a wearable device, wherein the test application has been formed using previously collected data that describe the movement of a person performing the predetermined action; computer readable program code that determines whether the movement data match the predetermined action in view of the classification; computer readable program code that receives output of a body-aware application that detects and responds to human movement; computer readable program code that compares the output of the body-aware application with the classification; and computer readable program code that provides an indication of the comparing of the output of the body-aware application and the classification.

A further aspect of the invention provides a method, comprising: receiving movement data that describe the movement of a person performing a predetermined action; receiving an identification of the predetermined action; training, using a processor, a three dimensional model for identifying the predetermined action using the movement data; forming, using the processor, an application program interface (API) for a classifier using the three dimensional model; and providing the API to an API library for inclusion in a test application which evaluates performance of a body-aware application.

For a better understanding of exemplary embodiments of the invention, together with other and further features and advantages thereof, reference is made to the following description, taken in conjunction with the accompanying drawings, and the scope of the claimed embodiments of the invention will be pointed out in the appended claims.

BRIEF DESCRIPTION OF THE SEVERAL VIEWS OF THE DRAWINGS

FIGS. 1A and 1B, illustrates differences between conventional software testing suites and body aware software testing suites.

DETAILED DESCRIPTION

Figure 1:
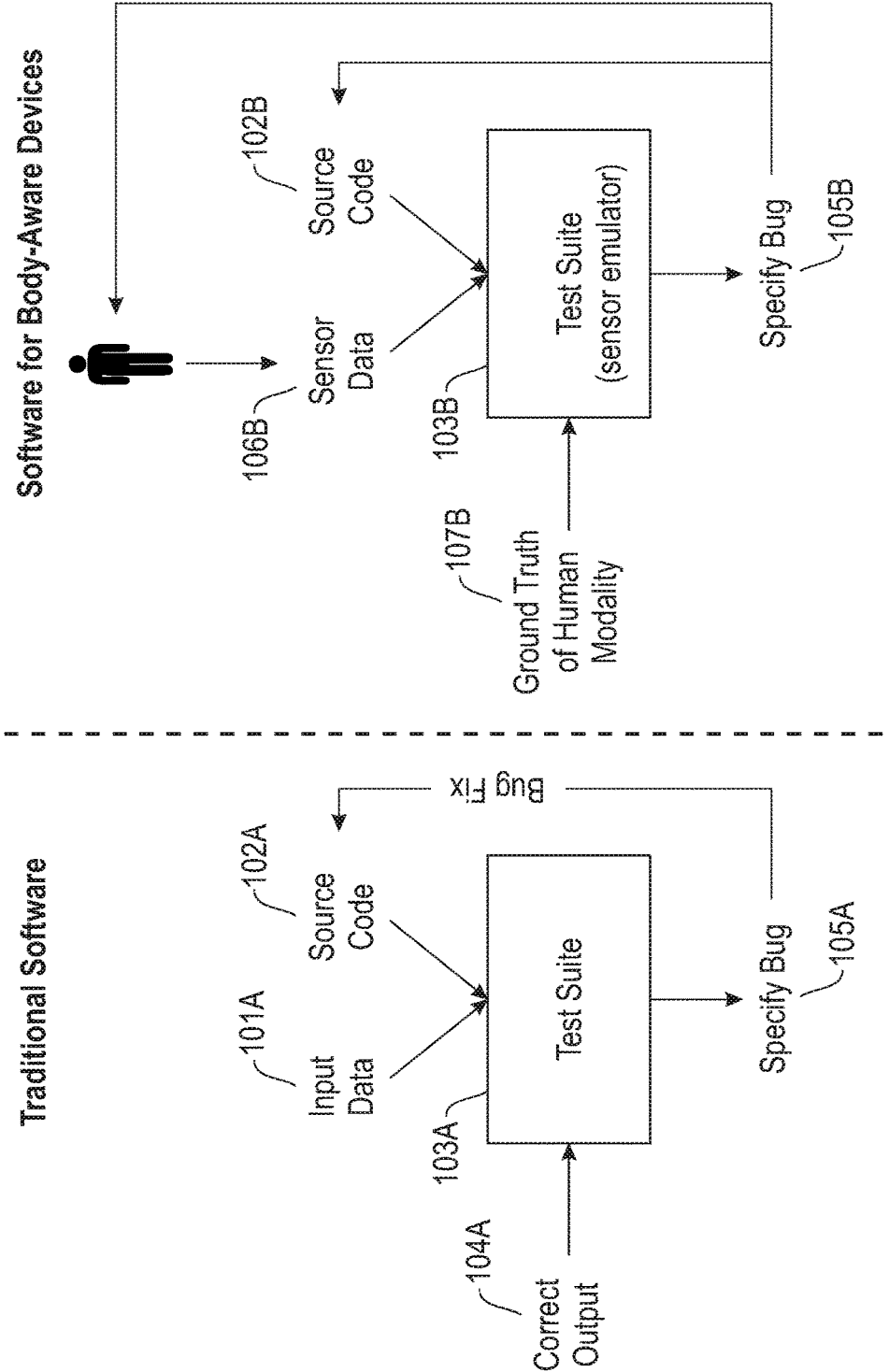
FIG. 1, which includes

It will be readily understood that the components of the embodiments of the invention, as generally described and illustrated in the figures herein, may be arranged and designed in a wide variety of different configurations in addition to the described exemplary embodiments. Thus, the following more detailed description of the embodiments of the invention, as represented in the figures, is not intended to limit the scope of the embodiments of the invention, as claimed, but is merely representative of exemplary embodiments of the invention.

Reference throughout this specification to "one embodiment" or "an embodiment" (or the like) means that a particular feature, structure, or characteristic described in connection with the embodiment is included in at least one embodiment of the invention. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in at least one embodiment. In the following description, numerous specific details are provided to give a thorough understanding of embodiments of the invention. One skilled in the relevant art may well recognize, however, that embodiments of the invention can be practiced without at least one of the specific details thereof, or can be practiced with other methods, components, materials, et cetera. In other instances, well-known structures, materials, or operations are not shown or described in detail to avoid obscuring aspects of the invention.

The illustrated embodiments of the invention will be best understood by reference to the figures. The following description is intended only by way of example and simply illustrates certain selected exemplary embodiments of the invention as claimed herein. It should be noted that the flowchart and block diagrams in the figures illustrate the architecture, functionality, and operation of possible implementations of systems, apparatuses, methods and computer program products according to various embodiments of the invention. In this regard, each block in the flowchart or block diagrams may represent a module, segment, or portion of code, which comprises at least one executable instruction for implementing the specified logical function(s).

It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Specific reference will be made here below to FIGS. 1-4. It should be appreciated that the processes, arrangements and products broadly illustrated therein can be carried out on, or in accordance with, essentially any suitable computer system or set of computer systems, which may, by way of an illustrative and non-restrictive example, include a system or server such as that indicated at 12' in FIG. 4. In accordance with an example embodiment, most if not all of the process steps, components and outputs discussed with respect to FIGS. 1-3 can be performed or utilized by way of a processing unit or units and system memory such as those indicated, respectively, at 16' and 28' in FIG. 4, whether on a server computer, a client computer, a node computer in a distributed network, or any combination thereof.

As shown in FIG. 1A, input data 101A are operated on by source code 102A provided to a test suit 103A. This permits the test suite 103A to work on the input data, e.g., simulated key strokes, touch screen inputs, etc., and compare the output of the source code to a known expected or correct output 104A. If variances are found, a bug 105A may be specified and used to alter the source code 102A appropriately.

However, body-aware device applications create certain issues that require modification of this paradigm. Specifically, there is a difficulty introduced in terms of how to obtain a ground truth as to what represents the correct output, e.g., what represents the appropriate response to various sensor input data. Moreover, there is a difficulty introduced in terms of how to find bugs in an automated way, e.g., identifying what the test suite should entail. Furthermore, there is a difficulty introduced in differentiating between a bug in the body-aware application and a problem with the input sensor data, e.g., incorrect gesture performance leading to improper input.

As illustrated in FIG. 1B, while source code 102B is still present for the body-aware application, the input data are sensor data 106B and therefore are dependent on human activity and sensor type, which may vary. For example, different users may perform different input actions, e.g., hand movements, arm movements, leg movements, eye movements, etc., in various ways while expecting the same output from the body-aware application. If these variances produce outputs that are indicated as bugs or errors, the body-aware software may be incorrectly considered to have a bug 105B that needs to be addressed, whereas the real issue is with the human input. Conversely, slight differences in performance by the user, e.g., of a yoga pose, exercise movement, or the like may not vary significantly in terms of the available sensor data 106B that are input to the test suite 103B; however, these smaller variances may be considered important and thus should be detected by the body-aware application, where lack of detection should be reported as a bug 105B.

In contrast to identifying a correct output in response to a known input such as an expected keystroke or an expected touch screen input, which is straightforward, to identify an appropriate response of software to a performed gesture or body movement is a significant task. This is because, among other things, humans vary in size, shape, mobility and the like, and thus can be expected to provide varying sensor data 106B as input to the test suite. Identifying what and how much tolerance to expect is a major issue in identifying proper performance of a body-aware application.

An embodiment therefore utilizes identification of a ground truth input as detected by another modality (sensor or sensor suite) as a mechanism for generating a correct output 107B using a companion (test) application, which then may be used for testing the body-aware application's output (i.e., by comparison). This correct output 107B is provided to the test suite 103B in order to test the body-aware application's output and specify a bug 105B if there is a variance from the companion application's output. This also helps resolve, in an automated way, how a potential bug should be addressed, e.g., via identification in an actual bug and subsequent modification of the source code 102B and/or via identification of an errant human input, and subsequent modification of the human input generating the sensor data 106B.

Figure 2:
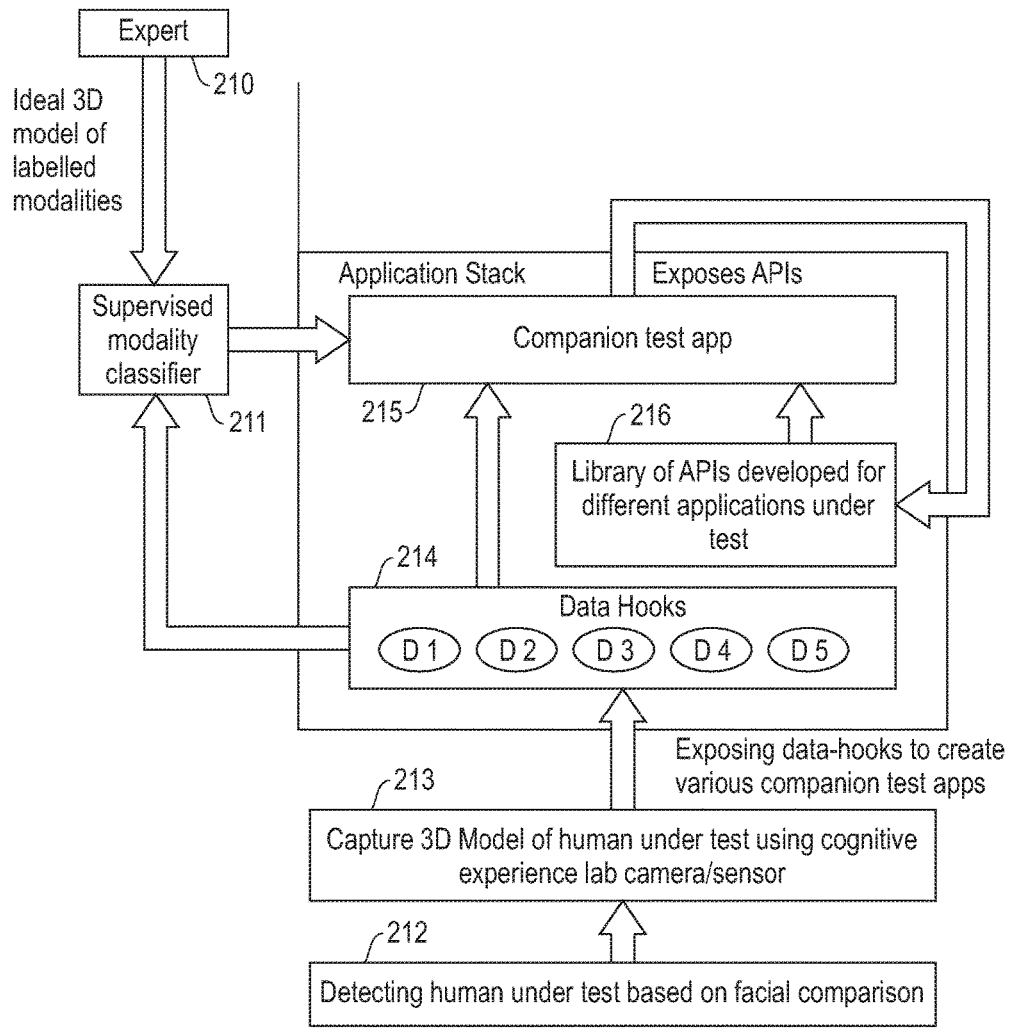
FIG. 2 illustrates an outline of forming a companion application for testing a body-aware application.

As illustrated in FIG. 2, an embodiment utilizes a testing environment to create a companion application, and thus expected output, based on performance of a human's (e.g., a person's) movement that may be used to evaluate the performance of an application under test (AUT), i.e., a body-aware application.

By way of specific example, the testing environment may be a room that accommodates one or more people, and thus a detection of the human under text (HUT) is made at 212 using a detection mechanism, e.g., facial comparison or other biometric identification. The testing environment obtains image data as input and applies a facial comparison on various humans in the environment to identify a target of focus for capturing data.

Once a HUT has been identified, an accurate three-dimensional (3D) model of the HUT is formed at 213. For example, multiple cameras within the environment, depth sensors, and audio devices capture a 3D model of the HUT in terms of position. The 3D model is specified for example as a wire frame for each instant of time as the HUT moves about.

At 214 data hooks (D1-D5) are exposed for the HUT 3D model. By way of example, the HUT is identified and computations are made on the 3D model of the HUT to provide data hooks specifying many details regarding position, orientation, velocity, etc., of different body parts of the HUT. As a specific example, for a weight training application, relevant data hooks may include angle and position of the wrist and biceps muscles. For a yoga application, the relevant data hooks might be the relative position of various body parts to one another as well as contact position(s) with the floor or a yoga mat that senses contact. Thus, data hooks may represent a stream of 3D coordinates and Euler angles of a particular limb (e.g., left foot) for a given modality. These data hooks do not detect specific modalities but rather provide the data required to detect a large class of modalities, which will be used in testing a body-aware application (AUT), as further described herein.

An embodiment constructs a companion application using the data hooks (D1-D5). The companion application is used to compare performance with an AUT in order to identify discrepancies with the output of the AUT as compared to the companion application.

Input, such as a list of expected activity modalities, which the AUT is designed to monitor and detect, are provided to the companion application, as well as the data hooks (D1-D5) produced from monitoring of the HUT in the environment. The output of the companion application is, based on the data hooks (D1-D5), distinguishes between the different modalities in the list, i.e., the goal is to define the functionality of the ideal AUT performance, the ground truth.

By way of example, a developer will identify the data hooks (e.g., from among D1-D5) that are relevant to the classification problem at hand, i.e., distinguishing between the modalities that are to be detected by the AUT. The developer writes a classifier that computes on the subscribed data hooks and detects either one of the activity modalities or none.

A library of APIs is provided at 216. Each companion application will expose its modality classifiers through APIs. For example, in the case of a weight training modality, a companion application may return a result of true in response to detecting input data of a specified limb being at a particular angle at a particular time. If a developer needs to build a new companion application specific to a new AUT, then the developer may use the existing APIs in the library as building blocks. The library of APIs may continue to grow over time.

An embodiment also provides an automated approach to developing a companion test application. For example, an embodiment provides for using existing data hooks (e.g., D1-D5) and/or APIs to build a customized companion application in an automated way.

In this approach, an expert performs different modalities, e.g., a movement, a posture, etc., and these are labeled. To cover the space of different users (e.g., body type, flexibility, etc.), multiple experts may be used to provide expert data 210.

This expert modality performance is monitored to produce movement data, e.g., regarding the movements, postures, etc., to form expert data 210, as for example detected using one or more sensors within the environment. The testing environment may include, but is not limited to, sensors that detect audio, touch, and image data.

The expert data 210 is used to train a supervised classifier at 211 to automatically detect the modalities performed by the expert based on relevant features of the HUT 3D model(s). Based on the trained classifier, a companion test application 215 is built and released to an application stack.

The companion test application 215 has a classifier that is trained with the supervised data from an expert (or experts) performing the modality. In cases where the companion test application is automatically generated, the expert and the developer may manually verify that the accuracy of the classifier is as desired. In particular, a testing phase may be conducted to quantify the accuracy of the companion application 215 prior to using it to test an AUT.

Figure 3:
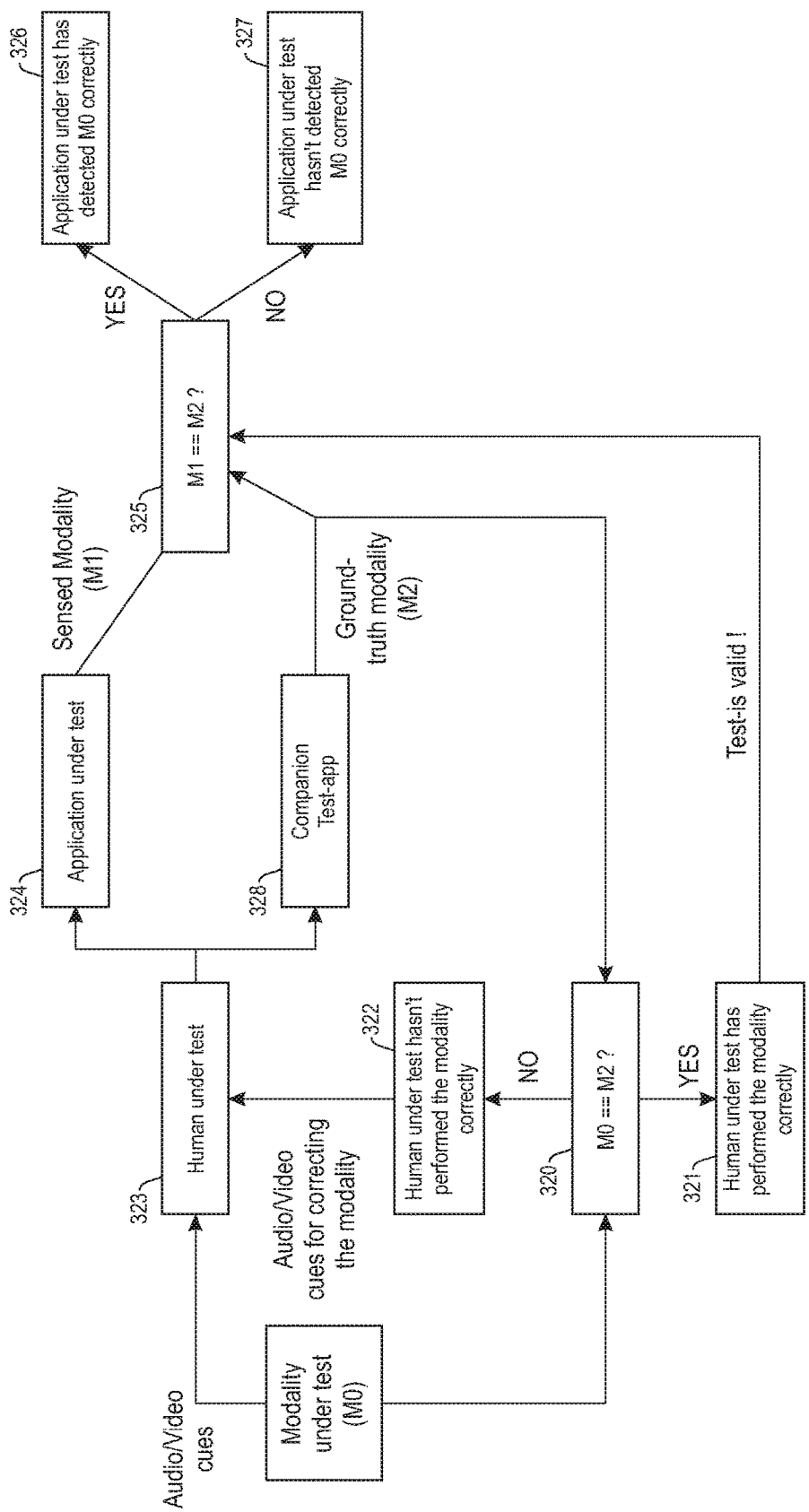
FIG. 3 illustrates an example method of testing a body-aware application using a companion application.

FIG. 3 outlines an example method of employing a companion application to evaluate or test and AUT. An embodiment is capable of detecting HUT errors, as opposed to AUT errors or bugs.

For example, as a HUT enters the testing environment with a wearable device containing an AUT, the HUT launches the AUT. The companion application is configured with the modalities of the AUT to be tested. Audio and/or visual cues are provided to the HUT at 323 to perform a first modality (M0).

The HUT attempts to perform modality M0 and the companion application, using input data from the testing environment (e.g., camera data), determines the modality (M2) actually performed by the HUT. An embodiment determines at 320 if the modality (M2) actually performed by the HUT is equivalent to the expected modality (M0). If so, the HUT has performed modality MO in an acceptable fashion, as indicated at 321, and the testing of the AUT may proceed. Otherwise, as indicated at 322, the HUT has not performed modality M0, and audio and/or visual cues or coaching are provided to the HUT in order to correct M2 to be equivalent to M0, as determined by the companion application.

An embodiment may use valid HUT performance of modality M0 to test the AUT for runtime errors. If there is no error in the HUT modality performance, as determined at 320, an embodiment queries the AUT on the detected modality (M1), i.e., the modality sensed by the AUT of the HUT performance of modality MO.

The AUT outputs the sensed modality M1 and this is compared to the companion application's output of M2, i.e., the ground truth of the modality that was performed by the HUT. Modalities M1 and M2 are compared for equivalence, as illustrated at 325. If equivalent, then the AUT has detected the modality M0 correctly, whereas a lack of equivalence indicates a runtime error in the AUT, as opposed to an error in the performance of modality M0 by the HUT.

An embodiment allows for testing of an AUT through various modalities. In each, there is a determination if the HUT is faithfully executing the modality, followed by a determination if the AUT is capable of detecting the modality. This ordering may be reversed.

An embodiment therefore provides a testing environment that is used to collect data on human(s) performance of various modalities (positions, postures, etc.) that are relevant to the performance of a body-aware application, e.g., a smart watch application. The human performance data may be used as input to a body aware application as well as a companion application. The output of the companion application and the body-aware application are compared, providing an indication as to whether the body-aware application is faithfully detecting the various modalities.

The various embodiments may be implemented using various computing devices in order to perform the functionality described herein.

Figure 4:
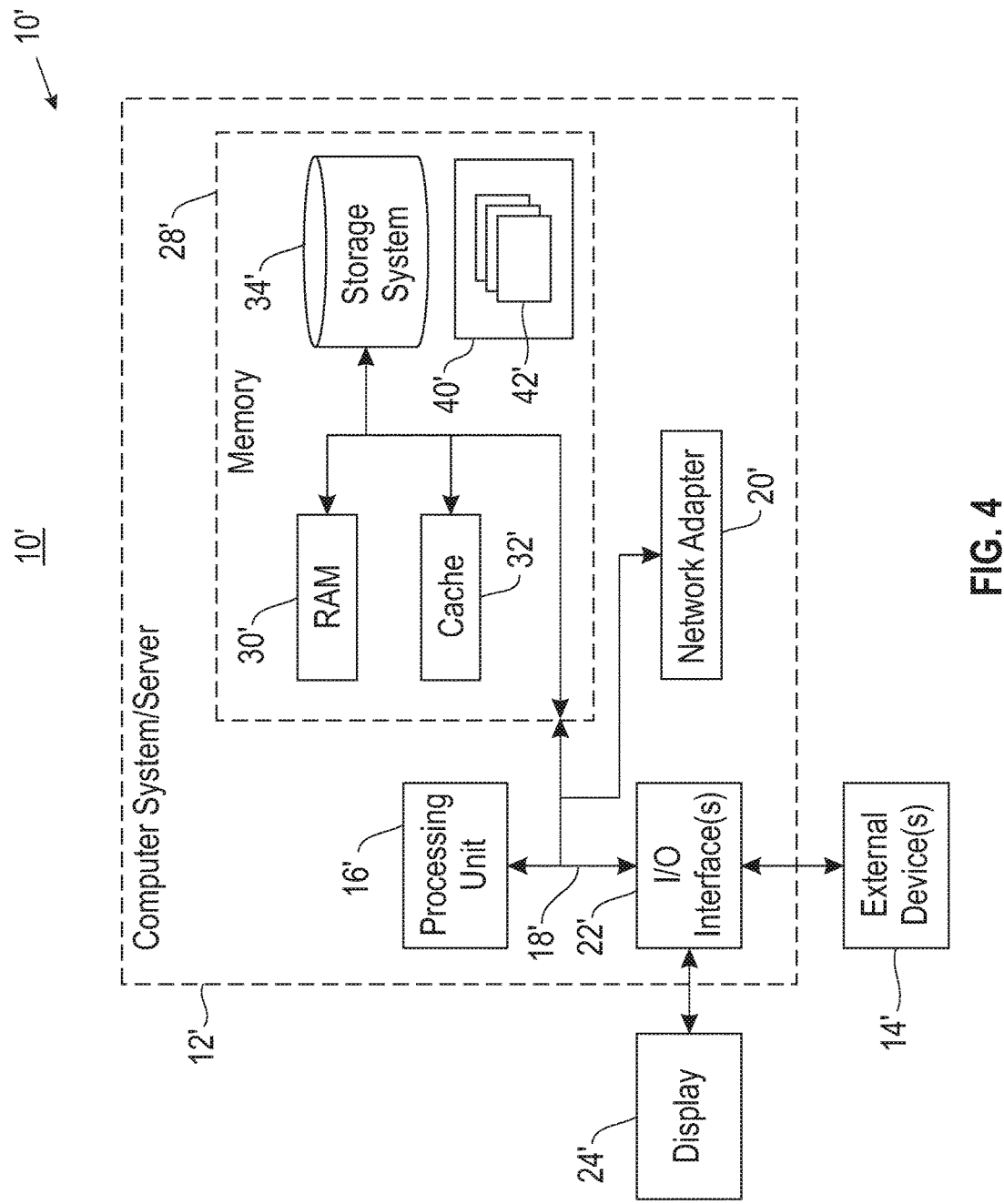
FIG. 4 illustrates a computer system.

As shown in FIG. 4, computer system/server 12' in computing node 10' is shown in the form of a general-purpose computing device. The components of computer system/server 12' may include, but are not limited to, at least one processor or processing unit 16', a system memory 28', and a bus 18' that couples various system components including system memory 28' to processor 16'. Bus 18' represents at least one of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12' typically includes a variety of computer system readable media. Such media may be any available media that are accessible by computer system/server 12', and include both volatile and non-volatile media, removable and non-removable media.

System memory 28' can include computer system readable media in the form of volatile memory, such as random access memory (RAM) 30' and/or cache memory 32'. Computer system/server 12' may further include other removable/non-removable, volatile/non-volatile computer system storage media. By way of example only, storage system 34' can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18' by at least one data media interface. As will be further depicted and described below, memory 28' may include at least one program product having a set (e.g., at least one) of program modules that are configured to carry out the functions of embodiments of the invention.

Program/utility 40', having a set (at least one) of program modules 42', may be stored in memory 28' (by way of example, and not limitation), as well as an operating system, at least one application program, other program modules, and program data. Each of the operating systems, at least one application program, other program modules, and program data or some combination thereof, may include an implementation of a networking environment. Program modules 42' generally carry out the functions and/or methodologies of embodiments of the invention as described herein.

Computer system/server 12' may also communicate with at least one external device 14' such as a keyboard, a pointing device, a display 24', etc.; at least one device that enables a user to interact with computer system/server 12'; and/or any devices (e.g., network card, modem, etc.) that enable computer system/server 12' to communicate with at least one other computing device. Such communication can occur via I/O interfaces 22'. Still yet, computer system/server 12' can communicate with at least one network such as a local area network (LAN), a general wide area network (WAN), and/or a public network (e.g., the Internet) via network adapter 20'. As depicted, network adapter 20' communicates with the other components of computer system/server 12' via bus 18'. It should be understood that although not shown, other hardware and/or software components could be used in conjunction with computer system/server 12'. Examples include, but are not limited to: microcode, device drivers, redundant processing units, external disk drive arrays, RAID systems, tape drives, and data archival storage systems, etc.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure.

Although illustrative embodiments of the invention have been described herein with reference to the accompanying drawings, it is to be understood that the embodiments of the invention are not limited to those precise embodiments, and that various other changes and modifications may be affected therein by one skilled in the art without departing from the scope or spirit of the disclosure.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method, comprising:
receiving movement data describing physical movement of a person performing a predetermined action;
generating, using a processor, classification of the movement data using a test application that predicts output of a wearable device, wherein the test application has been formed using previously collected data that describe the movement of a person performing the predetermined action;
determining, using the processor, whether the movement data match the predetermined action in view of the classification;
receiving output of a body-aware application that detects and responds to human movement;
comparing, using the processor, the output of the body-aware application with the classification; and
providing, using the processor, an indication of the comparing of the output of the body-aware application and the classification.

2. The method of claim 1, wherein
the indication indicates the output of the body-aware application and the classification do not match.

3. The method of claim 1, further comprising:
determining that the movement data do not match the predetermined action based upon the classification; and
providing a notification thereof.

4. The method of claim 3, wherein the notification comprises a corrective instruction for performing the movement data.

5. The method of claim 1, further comprising:
receiving the previously collected data that describes the movement of a person performing the predetermined action;
classifying the previously collected data using a classifier; and
providing an application program interface (API) to the test application utilizing the classifying of the previously collected data.

6. The method of claim 5, further comprising storing the API in an API library.

7. The method of claim 5, wherein the previously collected data that describe the movement of a person performing the predetermined action comprise data derived from a plurality of human experts performing the predetermined action.

8. The method of claim 1, wherein the generating the classification of the movement data using a test application comprises using a three dimensional (3D) model to compare 3D data of the movement data to a model attribute formed from previously obtained 3D movement data.

9. The method of claim 1, wherein the body-aware application is disposed within a wearable device worn by a person performing the predetermined action.

10. The method of claim 1, wherein the body-aware application is disposed within a device onto which a person stands while performing the predetermined action.

11. An apparatus, comprising:
at least one processor; and
a computer readable storage medium having computer readable program code embodied therewith and executable by the at least one processor, the computer readable program code comprising:
computer readable program code that receives movement data describing physical movement of a person performing a predetermined action;
computer readable program code that generates classification of the movement data using a test application that predicts output of a wearable device, wherein the test application has been formed using previously collected data that describe the movement of a person performing the predetermined action;
computer readable program code that determines whether the movement data match the predetermined action in view of the classification;
computer readable program code that receives output of a body-aware application that detects and responds to human movement;
computer readable program code that compares the output of the body-aware application with the classification of the movement of the companion test application; and
computer readable program code that provides an indication of the comparing of the output of the body-aware application and the classification.

12. A computer program product, comprising:
a computer readable storage medium having computer readable program code embodied therewith, the computer readable program code being executable by a processor and comprising:
computer readable program code that receives movement data describing physical movement of a person performing a predetermined action;
computer readable program code that generates classification of the movement data using a test application that predicts output of a wearable device, wherein the test application has been formed using previously collected data that describe the movement of a person performing the predetermined action;
computer readable program code that determines whether the movement data match the predetermined action in view of the classification;
computer readable program code that receives output of a body-aware application that detects and responds to human movement;
computer readable program code that compares the output of the body-aware application with the classification; and
computer readable program code that provides an indication of the comparing of the output of the body-aware application and the classification.

13. The computer program product of claim 12, wherein: the indication indicates the output of the body-aware application and the classification do not match.

14. The computer program product of claim 12, further comprising:
computer readable program code that determines that the movement data do not match the predetermined action using the classification; and
computer readable program code that provides a notification thereof.

15. The computer program product of claim 14, wherein the notification comprises a corrective instruction for performing the movement data.

16. The computer program product of claim 12, further comprising:
computer readable program code that receives the previously collected data that describes the movement of a person performing the predetermined action;
computer readable program code that classifies the previously collected data; and
computer readable program code that provides an application program interface (API) to the test application utilizing the classifying of the previously collected data.

17. The computer program product of claim 16, further comprising computer readable program code that stores the API in an API library.

18. The computer program product of claim 16, wherein the previously collected data that describe the movement of a person performing the predetermined action comprise expert movement data derived from a plurality of human experts performing the predetermined action.

19. The computer program product of claim 12, wherein the computer readable program code that generates the classification of the movement data using a test application comprises computer readable program code that uses a three dimensional (3D) model to compare 3D data of the movement data to a model attribute formed from previously obtained 3D movement data.

20. A method, comprising:
receiving movement data that describe the movement of a person performing a predetermined action;
receiving an identification of the predetermined action;
training, using a processor, a three dimensional model for identifying the predetermined action using the movement data;
forming, using the processor, an application program interface (API) for a classifier using the three dimensional model; and
providing the API to an API library for inclusion in a test application which evaluates performance of a body-aware application.

* * * * *